United States Patent
Schmieding et al.

(10) Patent No.: US 10,973,621 B2
(45) Date of Patent: Apr. 13, 2021

(54) GRAFT COMPRESSION AND SIZING TUBES

(71) Applicant: Arthrex, Inc., Naples, FL (US)

(72) Inventors: Reinhold Schmieding, Naples, FL (US); Adrian Wilson, Basingstoke (GB); Dean Acker, Naples, FL (US); Jacob A. Jolly, Naples, FL (US)

(73) Assignee: ARTHREX, INC., Naples, FL (US)

( * ) Notice: Subject to any disclaimer, the term of this patent is extended or adjusted under 35 U.S.C. 154(b) by 1050 days.

(21) Appl. No.: 14/814,826

(22) Filed: Jul. 31, 2015

(65) Prior Publication Data

US 2017/0027684 A1 Feb. 2, 2017

(51) Int. Cl.
*A61F 2/08* (2006.01)

(52) U.S. Cl.
CPC .................. *A61F 2/0805* (2013.01)

(58) Field of Classification Search
CPC ................................................. A61F 2/0805
See application file for complete search history.

(56) References Cited

U.S. PATENT DOCUMENTS

| | | | |
|---|---|---|---|
| 4,129,066 A * | 12/1978 | Corley | A47J 43/16 99/345 |
| 5,251,642 A | 10/1993 | Handlos | |
| 5,254,101 A * | 10/1993 | Trombley, III | A61M 5/14546 604/187 |
| 5,415,651 A | 5/1995 | Schmieding | |
| 5,570,706 A | 11/1996 | Howell | |
| 5,671,695 A * | 9/1997 | Schroeder | A61B 17/1714 128/897 |
| 6,019,767 A | 2/2000 | Howell | |
| 6,203,572 B1 | 3/2001 | Johnson et al. | |
| 6,254,604 B1 | 7/2001 | Howell | |
| 6,575,204 B1 * | 6/2003 | Godfrey | A47J 37/106 141/1 |
| 6,666,832 B1 | 12/2003 | Carranza et al. | |
| 6,796,977 B2 | 9/2004 | Yap et al. | |
| 7,014,618 B2 | 3/2006 | Carranza et al. | |
| 7,740,657 B2 | 6/2010 | Brown, Jr. et al. | |
| 2003/0069545 A1 * | 4/2003 | Arm | A61B 17/8822 604/218 |
| 2008/0243248 A1 | 10/2008 | Stone et al. | |
| 2010/0036432 A1 * | 2/2010 | Ely | A61B 17/7032 606/301 |
| 2012/0041388 A1 * | 2/2012 | Blomquist | A61D 7/00 604/227 |
| 2012/0059469 A1 | 3/2012 | Myers et al. | |

(Continued)

FOREIGN PATENT DOCUMENTS

WO WO 96/03086 2/1996

OTHER PUBLICATIONS

Dupy Synthes's "Graft Preparation System" DuPuy Synthes Mar. 19, 2015, pp. 1-2.

(Continued)

*Primary Examiner* — Jerrah Edwards
*Assistant Examiner* — Christine L Nelson
(74) *Attorney, Agent, or Firm* — Carlson, Gaskey & Olds (57) ABSTRACT

Graft compression and sizing tubes, methods of graft sizing and compression using such graft tubes, and kits of graft tubes are disclosed. A graft tube aids in graft preparation for a surgery by quickly and consistently compressing a graft to a desired diameter and measuring the length of the graft.

23 Claims, 5 Drawing Sheets

(56) References Cited

U.S. PATENT DOCUMENTS

2012/0083808 A1* 4/2012 Shriver ................ A61B 17/11
606/153
2014/0031932 A1 1/2014 Myers

OTHER PUBLICATIONS

Arthrex "Graft Sizing Block" Apr. 4, 2015, 1 page.
Biotek "Graft Sizing Block" Ahmedabad, India, Apr. 6, 2015, 4 pages.
Cayenne Medical "Transtibial Surgical Technique Guide" Scottsdale, AZ, 8 pages.
Linvatec'S SE$^{TM}$ "Graft Tensioning System" Linvatec Corporation, a subsidiary of ConMed Corporation 2003, 2004, Largo FL, 11 pages.
Smith & Nephew "Complete Solutions for Knee Arthroscopy" Smith & Nephew, Inc., Andover MA, Oct. 2012, 34 pages.

* cited by examiner

GRAFT COMPRESSION AND SIZING TUBES

BACKGROUND

The present disclosure relates to surgical devices. In particular, the present disclosure relates to surgical devices and methods for use in connection with graft preparation and sizing.

SUMMARY

Graft tubes and methods of using graft tubes are disclosed. A graft tube can aid in graft preparation for surgery by compressing a graft to a desired diameter and measuring a length of the graft. Graft tubes can be full length, full circumference transparent tubes that can include an etched ruler to allow for visualization of a graft during diameter and length sizing. Transparent tubes can include a funneled entrance and an attachable handle, to allow ease of entry and compression of the graft. A graft tube can include a plurality of perforations to allow a graft to be hydrated or injected with biologics along its length. A tapered tip can allow for delivery of a graft directly into a prepared bone socket or tunnel.

A method of graft sizing and compressing is also disclosed. A graft may be loaded into a graft tube and inserted into a bone socket. Depending on the diameter of the graft, an appropriately sized graft tube can be selected for graft compression. A graft can be loaded into a graft tube via a funneled entrance and can be measured by an etched ruler on a graft tube body. A graft can be removed from the tube and resized if needed. After obtaining a graft of a desired length and diameter, hydrations or biologics can optionally be injected into the graft. A tapered tip of the graft tube can be placed at the bone socket entrance and the graft can be pulled from the graft tube and loaded into a surgical site.

A kit is also disclosed. In an embodiment, a kit can include a plurality of graft tubes having inner diameters of different sizes. A kit can further include one or more attachable handles that can be selectively attached to the graft tubes.

DETAILED DESCRIPTION

A variety of surgical treatments involve the reconstruction of ligaments using grafts, including arthroscopic shoulder surgery, knee ligament reconstruction techniques, etc. Various grafting materials have been used in ligament reconstructions, including autografts, allografts, xenografts, and synthetic materials. For example, a graft, such as a composite femoral bone/tendon allograft, can be prepared to have a diameter corresponding to the diameter of femoral and tibial sockets in an anterior cruciate ligament (ACL) replacement procedure. Alternatively, a graft can be prepared prior to bone sockets being drilled, and the bone sockets can subsequently be prepared to have a diameter corresponding to the diameter of the graft.

A graft tube can aid in graft preparation for a surgery by compressing a graft to a desired diameter and measuring or verifying the length of the graft. As detailed below, the graft tubes can be full length, full circumference transparent tubes that can include an etched ruler that allows for visualization of the graft during diameter and length sizing. A transparent graft tube can include a funneled entrance and an attachable handle and allow ease of entry and compression of the graft. The body of the graft tube can include a plurality of perforations to allow the graft to be hydrated or injected with biologics along its length, for example, along its entire length. A tapered tip can allow for delivery of the graft directly into the prepared bone socket.

Sets of graft sizing and compression tubes are also disclosed. A set includes at least the following elements: (i) translucent body of the tube to allow for visualization of the graft during sizing; (ii) tube allows for compression of the graft up to 2 mm; (iii) attachable pull handle for counter resistance; (iv) perforations to allow for injections of biologics or hydrations; (v) coned, smooth entrance to facilitate pulling graft into tube; and (vi) tapered exit to allow insertion into bone tunnel or joint.

Graft compression and sizing tubes facilitate graft compression, sizing, and/or preparation. The unique transparent tubes with an etched ruler allow visualization of the graft during diameter and length sizing. A funneled entrance and attachable handle ease the entry of grafts into the sizer, allowing compression of up to 2 mm. Small perforations in the graft tubes allow for hydration of the graft or injection of biologics along the entire length. The tapered tip allows for delivery of the graft directly into the tibial tunnel or medial portal.

Methods of sizing and/or preparing and/or compressing a graft are also disclosed. In an embodiment, depending on the diameter of a graft, an appropriately sized graft tube can be selected for graft compression. A graft can be loaded into a graft tube via the funneled entrance and can be measured by the etched ruler on the graft tube body. A graft can be removed from a graft tube and resized if needed. After obtaining a graft of the desired length and diameter, hydrations or biologics can optionally be injected into the graft. The tapered tip of a graft tube can be placed at the bone socket entrance, and a graft can be pulled from the graft tube and loaded into a surgical site.

Figure 1:
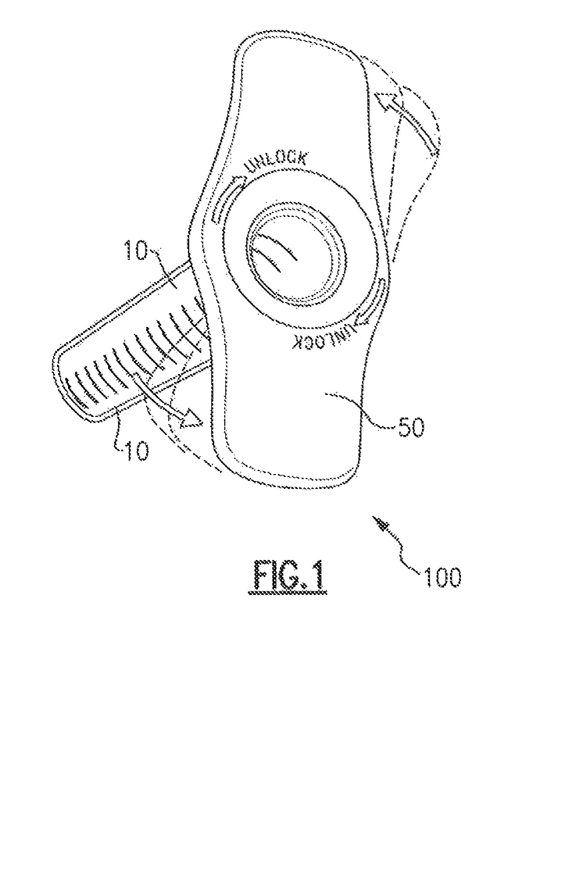
FIG. 1 is a perspective view of a graft tube assembly according to an exemplary embodiment.
Figure 2:
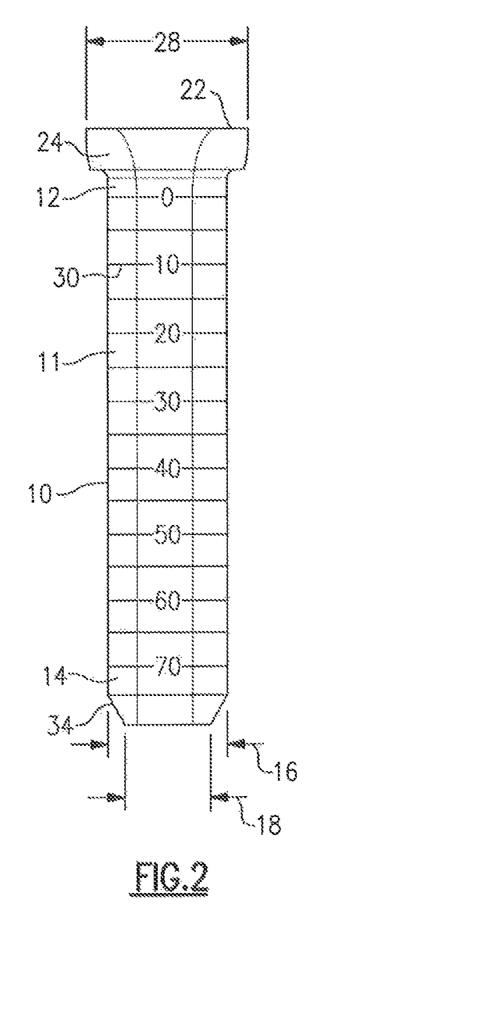
FIG. 2 is a side view of a graft tube of the graft tube assembly of FIG. 1.
Figure 8:
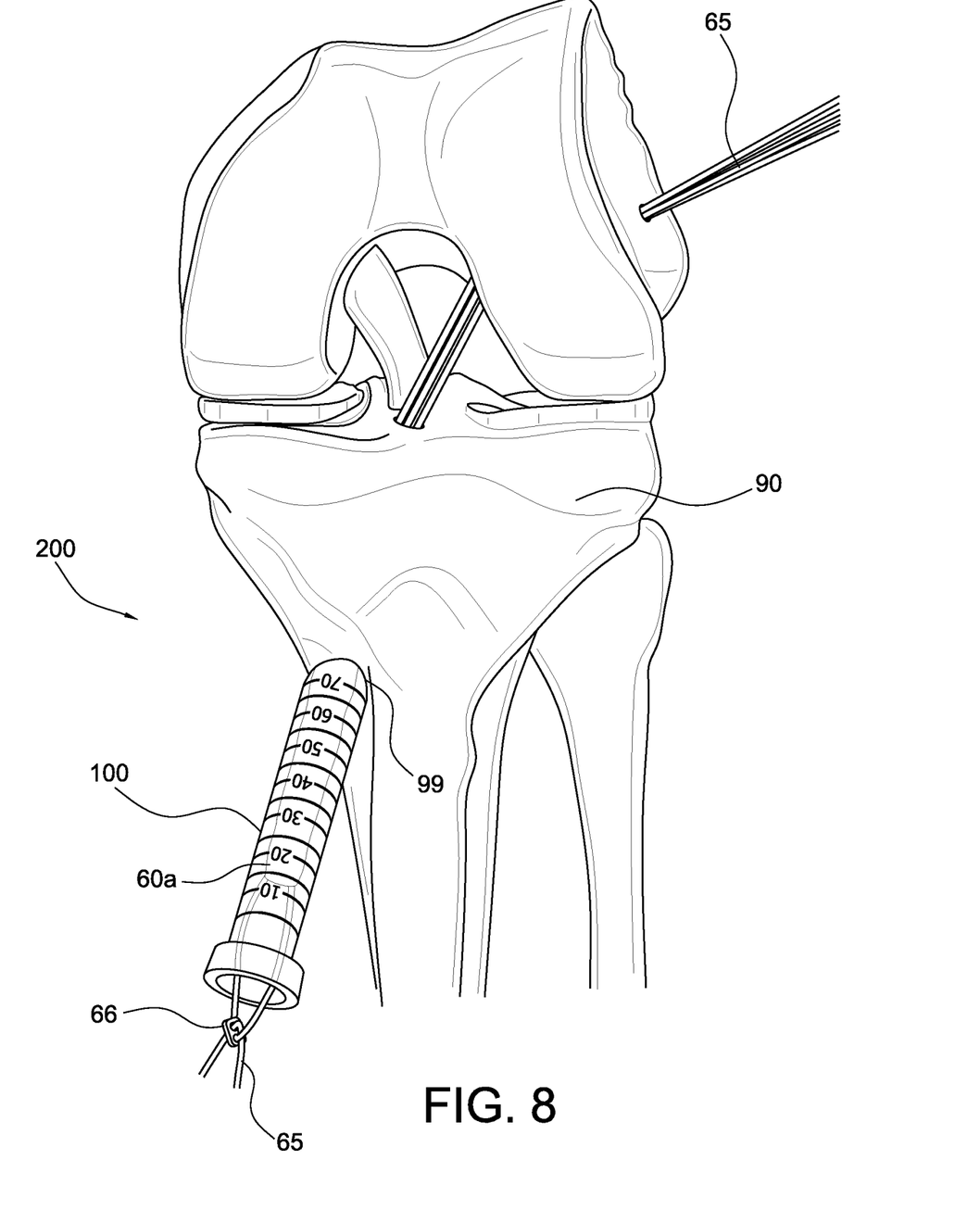
Figure 9:
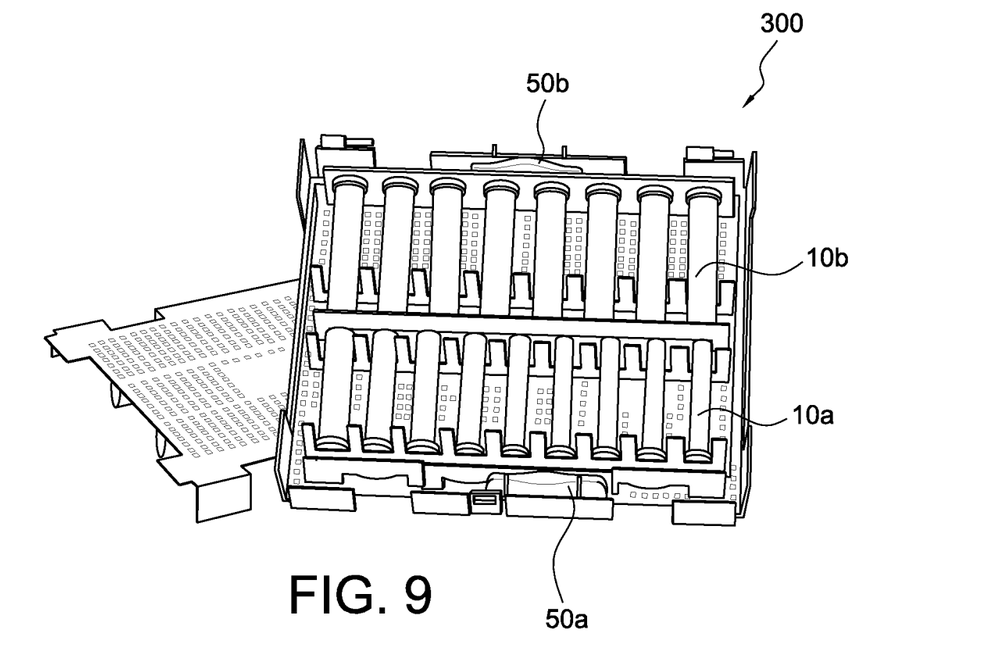
FIG. 9 illustrates a kit having a set of graft tubes and at least one attachable handle, according to an exemplary embodiment.
Figure 10:
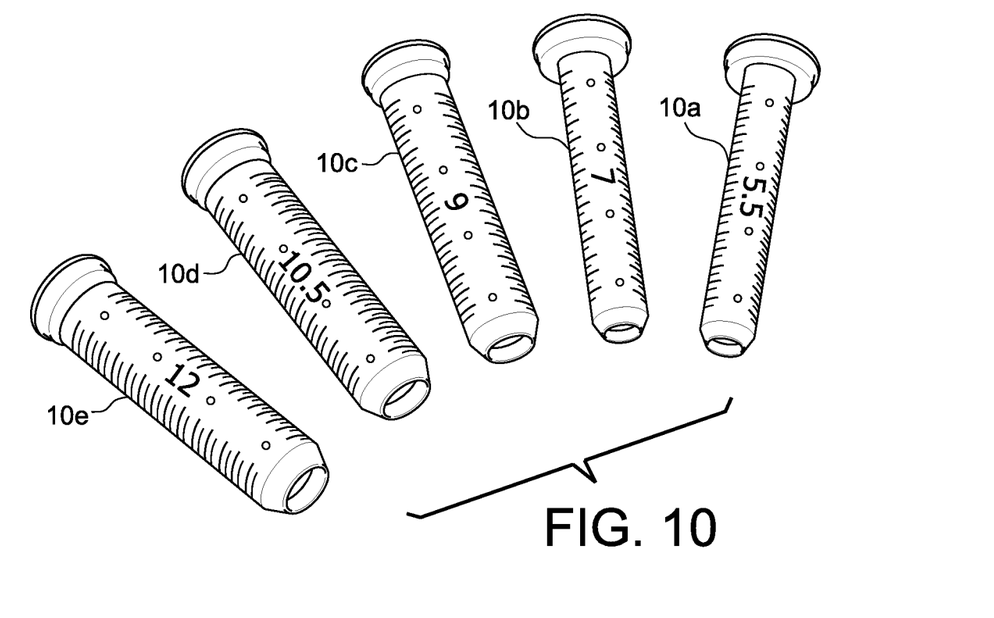
FIG. 10 illustrates graft tubes of various sizes and dimensions, according to an exemplary embodiment.

FIGS. 1-10 illustrate graft tube assemblies, systems, kits, and methods of the present disclosure. FIGS. 1 and 2 illustrate assembly 100 (graft tube assembly 100) formed of exemplary graft tube 10 and handle 50 to allow sizing and measuring of soft tissue 60 (graft 60). FIGS. 3-8 illustrate steps of an exemplary method of graft preparation (sizing and/or compression) of graft 60 with assembly 100, and tissue reconstruction with sized and/or compressed graft 60a, to achieve surgical repair 200. FIG. 9 illustrates a kit 300 having a set of graft tubes and one or more attachable handles, according to an exemplary embodiment. FIG. 10 illustrates graft tubes of various sizes and dimensions.

FIGS. 1 and 2 illustrate assembly 100 (graft tube assembly 100) formed of exemplary graft tube 10 and handle 50. Handle 50 may be an attachable handle. Graft tube 10 may have a body 11 having a proximal end 12 and a distal end 14. Body 11 can further have an outer diameter 16 and an inner diameter 18, where the inner diameter 18 defines a hollow tunnel through which soft tissue 60 (graft 60) passes.

Handle 50 may be an attachable handle, which is understood to refer to any handle that can be selectively secured to graft tube 10. Handle 50 enables easy application of a counter resistance when pulling graft 60 through graft tube 10. That is, when pulling graft 60 through graft tube 10, a force in the opposite direction may need to be applied in order to hold graft tube 10 in place. Handle 50 enables this counter resistance to be applied quickly and easily.

Figure 3:
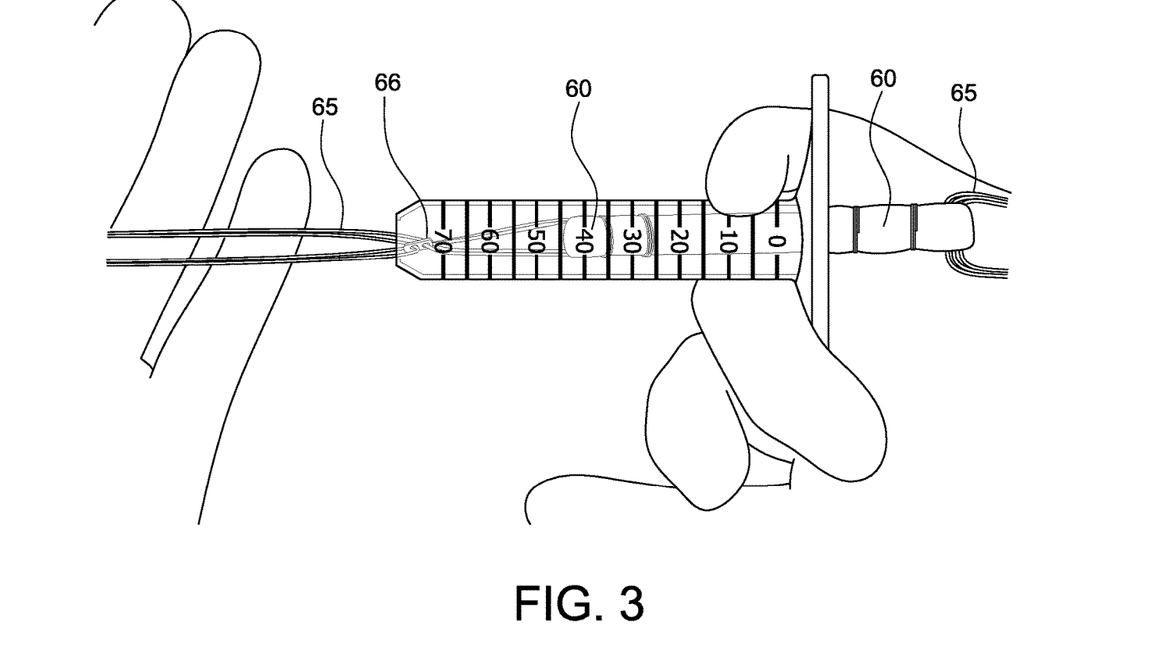
FIGS. 3-8 illustrate a method of surgery with the assembly of FIG. 1 and with a graft loaded into a graft tube.

Proximal end 12 of tube 10 can be configured to have a funneled entrance 22 to ease entry of a graft 60 into the tube. The funneled entrance 22 can be of any suitable size to facilitate loading the graft 60 into the tube, with the mouth of the funnel being wider than the inner diameter 18 of the graft tube. The mouth of the funnel can have any width up to and including the width of the outer diameter 16. The funneled entrance 22 also allows for grafts that are wider than the inner diameter 18 of the tube to be loaded into the tube and compressed. For example, the graft tube can compress a graft by up to 2 mm in diameter. In other embodiments, the graft tube can compress a graft by up to 1 mm, up to 1.5 mm, up to 2.5 mm, or up to 3 mm. In other embodiments, graft tubes do not compress the graft. Regardless of the amount of compression by a graft tube, the compression can be uniform for each graft passed into that graft tube, allowing for standardized graft diameters and for standardized bone socket sizing. FIG. 3 shows an example embodiment of the graft 60 partially loaded into the graft tube 10 of assembly 100.

FIGS. 1 and 2 illustrate proximal end 12 including a head 24 that is configured to accept an attachable handle 50. The head 24 can have a head diameter 28 that may be the same on all graft tubes to allow for the same attachable handle 50 to be used on graft tubes having different outer diameters. The attachable handle 50 can be attached and locked into place by turning it in one direction, and unlocked and detached by turning it in the opposite direction. In an embodiment of a kit (as shown in FIGS. 9 and 10, for example), graft tubes can have the same head diameter 28 to use the same attachable handle 50. In another embodiment, multiple attachable handles of the same size can be included in the kit. In another embodiment, the graft tubes in the kit can be configured to have heads with different head diameters, and the kit can further include at least one attachable handle for each different head diameter.

Body 11 of graft tube 10 can be made of a transparent material to allow viewing the graft 60 while the graft is in the graft tube. This allows the length of the graft 60 to be measured and/or verified prior to positioning/implanting the sized and compressed graft 60a into a bone socket or tunnel. The transparent material can be any suitable material that allows for a sufficiently solid body 11 and visualization of the graft 60.

Body 11 of graft tube 10 can include an etched ruler 30 to facilitate quick and consistent measurements. In an exemplary embodiment shown in FIG. 2, the transparent body 11 includes an etched ruler 30 that has markings ranging from 0 mm to 70 mm. Other embodiments (not shown) can have markings for any appropriate length. For example, a graft tube could have markings from 0-50 mm, 0-60 mm, 0-80 mm, 0-90 mm, 0-100 mm, or anything in between. Graft tubes could optionally have markings from 0 mm to greater 100 mm, or 0 mm to less than 50 mm as needed.

Figures 6, 7:
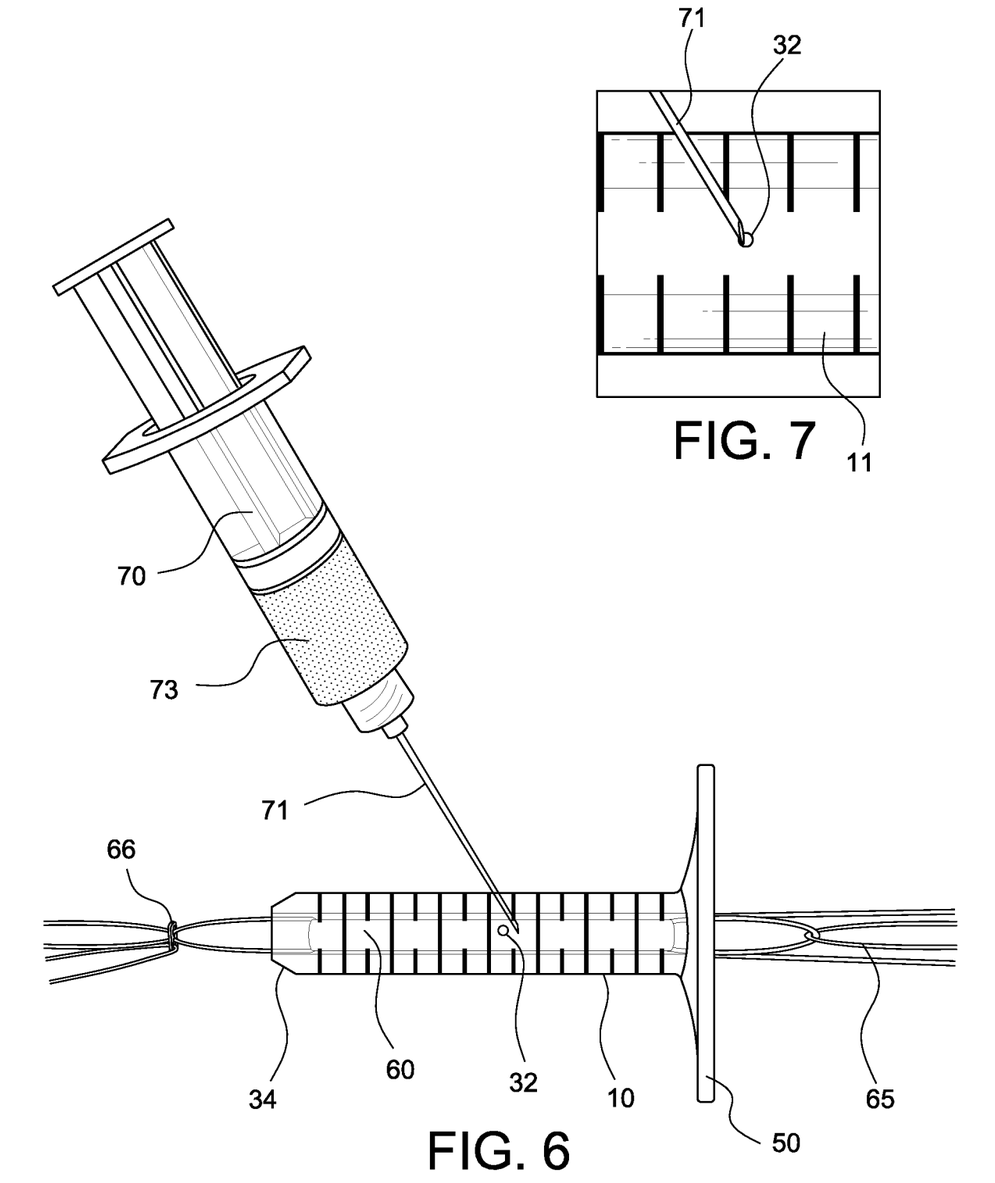

According to an exemplary embodiment and as shown in FIGS. 6 and 7, graft tubes 10 can include a plurality of perforations 32 spread along the length of the graft tube body 11. The perforations 32 can be sized to allow for a needle 71 of device 70 (for example, a syringe 70) to pass into the graft 60, 60a while the graft is positioned within the graft tube. The needle 71 can inject any suitable material 73 into the graft 60, 60a, for example the needle 71 can inject hydrations or biologics. The body 11 can include any number of perforations 32. Additionally, the perforations 32 can be spaced in any manner, for example, the perforations 32 can be spaced at regular intervals in a straight line, irregular intervals in a straight line, regular intervals anywhere around the circumference of the body 11, irregular intervals anywhere around the circumference of the body 11, or any other location on the body 11.

As shown in FIGS. 1-8, distal end 14 of graft tube 10 can have a tapered tip 34. The tapered tip 34 can be designed to at least partially fit within a bone socket or tunnel 99 formed within bone 90. For example, the tapered tip 34 of the graft tube 10 can be tapered to allow delivery of graft 60a directly into a bone socket. The tapered tip minimizes contact with skin or other possible contaminants. The degree of the taper can be any suitable degree that facilitates the goal of delivering the graft into a bone socket.

Figure 4:
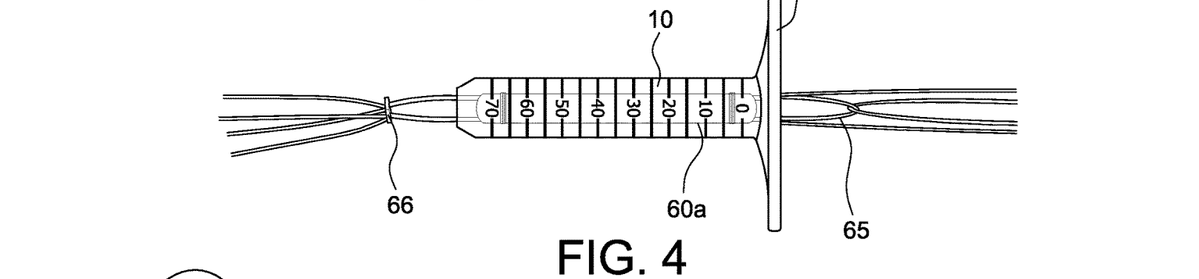
Figure 5:
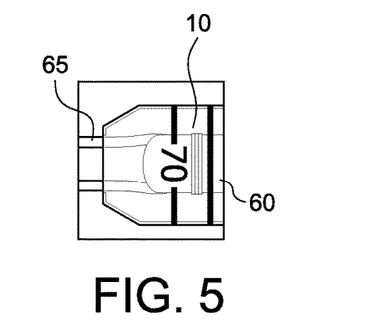

FIGS. 3-8 illustrate exemplary steps of a method of employing assembly 100 to measure and/or size and/or compress a graft 60. A graft 60 can be loaded into funneled entrance 22 of any of the example graft tubes described above, as shown in FIG. 3. The graft 60 can be pulled fully within the tube (as shown in FIGS. 4 and 5) such that one end of the graft 60 is resting at a 0 mm marking on the etched ruler of tube 10. If the inner diameter of the graft tube is less than the diameter of the graft, the act of pulling the graft 60 into the graft tube compresses the graft 60 by any of the amounts described above to achieve compressed graft 60a (FIG. 4). Compressed graft 60a has an overall outer diameter smaller than that of graft 60 by up to 2 mm.

The length of the graft can be measured and/or verified using the etched ruler 30. The tapered tip 34 of tube 10 can then be placed adjacent to a prepared bone socket 99 (for example, a tibial tunnel or socket 99 formed within tibia 90), and the compressed graft 60a can be pulled out of the graft tube 10 and into the bone socket 99, as shown in FIG. 8, to obtain repair 200. Alternatively, the tapered tip 34 can be placed at least partially within the bone socket 99.

If desired, prior to insertion of compressed graft 60a within tunnel or socket 99, material 73 may be provided to compressed graft 60a, for example, by insertion through the plurality of perforations 32 along the body 11 of tube 10, and as shown in FIGS. 6 and 7.

The graft tubes described above can be used in conjunction with any surgical procedure involving graft preparation and/or positioning/insertion. For example, a graft, such as a composite femoral bone/tendon allograft, can be prepared to have a diameter corresponding to the diameter of the femoral and tibial sockets in an ACL replacement procedure. Alternatively, a graft can be prepared prior to bone sockets being drilled, and the bone sockets can subsequently be prepared to have a diameter corresponding to the diameter of the graft.

The length of the graft can correspond to the sum of the lengths of the femoral and tibial sockets plus the joint space distance between the two socket openings. For example, assuming that the length a femoral socket is about 25 mm, the length of a tibial socket is about 25 mm, and the length between the two sockets is about 28 mm, the total length of the graft can be about (25+25+28) mm, or about 78 mm.

Graft 60 can be formed according to any means known in the art. In an exemplary embodiment, during preparation of a graft, the graft can be folded in half and whipstitched at a graft proximal end and distal bundle ends. The graft can be marked 25 mm from the graft proximal end, for example, corresponding to the depth of a femoral socket. A joint space length of 28 mm, for example, can be marked further down the graft. The two distal graft bundles are measured to 25 mm, for example, corresponding to the depth a tibial socket.

The ends of the graft can be securely whipstitched independently with one set of flexible materials (strands) and a second set of flexible materials (strands). The individual strands of the second set of strands can be visually distinguishable. The diameter can be measured by the graft tubes, and the length can additionally be measured and/or verified by the graft tubes. In another embodiment, the graft tube measurements can be conducted after affixing fixation devices (for example, buttons) and flexible strands (for example, sutures) to the graft, as needed for insertion and graft securing into bone. FIGS. 3-8 show a graft 60 with flexible strands 65 (sutures 65) and fixation devices 66 (buttons 66) already affixed to the graft 60.

In an exemplary method of using a graft tube 10 of surgical assembly 100, a graft can be loaded into the funneled entrance 22 of any of the example graft tubes described above. The graft 60 can be pulled fully within the tube such that one end of the graft is resting at a 0 mm marking on the etched ruler. If the inner diameter of the graft tube is less than the diameter of the graft, the act of pulling the graft into the graft tube compresses the graft by any of the amounts described above. The length of the graft can be measured and/or verified using the etched ruler 30. The tapered tip 34 can then be placed adjacent to a prepared bone socket, and the graft can be pulled out of the graft tube and into the bone socket. Alternatively, the tapered tip 34 can be placed at least partially within the bone socket.

In an exemplary embodiment, in addition to the method described above, prior to loading a graft into the funneled entrance 22 of any of the graft tubes, an appropriately sized graft tube can be selected from a set of graft tubes. Attachable handle 50 can then be attached to the selected graft tube.

In an exemplary method of using a graft tube, hydrations or biologics can be administered (e.g., injected) through the perforations 32 and into or onto the graft 60 prior to positioning the tapered tip 34 adjacent to or partially within a bone socket.

Exemplary kit 300 (FIG. 9) can include a plurality of graft tubes (for example, 10a, 10b . . . 10e, as shown in FIG. 10) having inner diameters of different sizes. For example, the kit can include two or more graft tubes, wherein the inner diameters of the graft tubes are different to facilitate preparing grafts having different diameters. In an exemplary embodiment, the kit can have a plurality of graft tubes with inner diameters ranging between 2 mm and 20 mm. The kit can include graft tubes with an inner diameter at each whole number within the range, for example 2 mm, 3 mm, 4 mm, and so forth up to 20 mm. Alternatively, the kit can additionally include half sizes, for example 2 mm, 2.5 mm, 3 mm, 3.5 mm, and so forth up to 20 mm. It is to be understood that any smaller range within this set can be appropriate. For example, a kit can have graft tubes ranging between 5 mm and 13 mm, and in another example, the kit having a range between 5 mm and 13 mm can further include half sizes. In the example embodiment shown in FIG. 9, kit 300 has 17 total graft tubes, with sizes ranging between 5 mm and 13 mm and including half sizes.

The kit 300 shown in FIG. 9 further includes two attachable handles 50a and 50b. Other size ranges may be appropriate according to the application. For example, a kit of graft tubes can have a range of inner diameters of 4-12 mm, 4-13 mm, 4-14 mm, 4-15 mm, 5-12 mm, 5-13 mm, 5-14 mm, 5-15 mm, 6-12 mm, 6-13 mm, 6-14 mm, 6-15 mm, and any other range having bounds between 2 mm and 20 mm.

A kit as described above can further include one or more attachable handles. The graft tubes of the kit can be configured to have a uniform head diameter 28, and in such a case, the kit can have only one attachable handle. Alternatively, the kit can include multiple attachable handles, any of which can be used with any of the graft tubes. In other embodiments, the graft tubes can have different head diameters. For example, approximately half of the graft tubes can have one head diameter and the remainder can have a different head diameter, and the kit can then include at least one attachable handle for each head diameter. In another embodiment, the set of graft tubes can have more than two different head diameters, and thus at least one attachable handle to correspond to each of the different head diameters.

In any of the example embodiments of a kit described above, the kit can further include a low profile sterilization tray.

One or more hydration or biological materials 73 such as blood, blood components, bone marrow aspirate (BMA), bone marrow concentrate, platelet rich plasma (PRP), calcium chloride, stem cells, growth factors (e.g., platelet derived growth factor (PDGF), vascular endothelial growth factor (VEGF), etc.), and combinations thereof may be administered to the graft (for example, injected), to further improve and accelerate incision and tissue healing. The plasma fractions may further include one or more vitamins such as vitamin E, vitamin A, and other retinoids. Alternatively, or additionally, non-vitamin anti-oxidants may be included in the biological material. Alternatively, a graft construct may be impregnated with such hydration and/or biological materials.

Flexible strands 65 of the graft construct 60, 60a of the present disclosure may be spliced—at least in part—in a manner similar to Arthrex ACL TightRope® technology, such as disclosed in U.S. Pat. Nos. 8,439,976 and 8,460,379, the disclosures of which are incorporated by reference in their entirety herein.

Flexible strands 65 may be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). FiberWire® suture (Arthrex, Inc.) is formed of an advanced, high-strength fiber material, namely UHMWPE, sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material.

Flexible strands 65 may be also in the form of flat suture tape (for example, a high strength suture tape, such as disclosed in U.S. Pat. No. 7,892,256) or a combination of suture and tape, a stiff material, or combination of stiff and flexible materials, depending on the intended application.

Fixation devices 66 may be buttons such as a RetroButton® (Arthrex), ACL Tightrope® or other suture loop/button constructs attached to the reinforced/compressed graft construct 66a to secure attachment to bone cortex (for example, the tibial and femoral sides in ACL reconstruction).

What is claimed is:
1. A graft tube assembly, comprising:
 a transparent body having a proximal end, a distal end, an outer diameter, and an inner diameter, wherein the inner diameter defines a hollowed tunnel configured to receive a graft;

an etched ruler on the transparent body;
a funneled entrance at the proximal end;
a tapered tip at the distal end; and
an attachable handle.

2. The graft tube assembly of claim 1, further comprising a plurality of perforations along a length of the transparent body.

3. The graft tube assembly of claim 1, wherein the inner diameter is between 2 mm and 20 mm.

4. The graft tube assembly of claim 1, wherein the inner diameter is between 5 mm and 13 mm.

5. The graft tube assembly of claim 1, further comprising a head at the proximal end configured to receive the attachable handle.

6. The graft tube assembly of claim 5, wherein the head has a diameter that is greater than the outer diameter of the transparent body.

7. The graft tube assembly of claim 1, wherein the etched ruler has markings from 0 mm to 100 mm.

8. The graft tube assembly of claim 1, wherein the graft tube compresses a graft up to 2 mm.

9. The graft tube assembly of claim 1, wherein the graft is a soft tissue graft.

10. The graft tube assembly of claim 1, wherein the attachable handle is rotatable in a first direction to lock the attachable handle to a head at the proximal end of the transparent body and is rotatable in a second, opposite direction to unlock the attachable handle from the head.

11. The graft tube assembly of claim 1, comprising:
a head disposed at the proximal end of the transparent body, the head including a head diameter that is greater than the outer diameter of the transparent body,
wherein the funneled entrance includes a mouth at a first end of the head and a second, opposite end that extends to the proximal end of the transparent body.

12. A method of preparing a graft, comprising:
loading a graft into the graft tube assembly of claim 1;
placing one end of the graft at a 0 mm marking on the etched ruler; and
measuring the length of the graft.

13. The method of claim 12, further comprising compressing the graft up to 2 mm while simultaneously measuring the length of the graft.

14. The method of claim 12, further comprising injecting a material into the graft.

15. The method of claim 12 further comprising placing the tapered tip adjacent to a bone socket; and pulling the graft into the bone socket.

16. The method of claim 14, wherein the material is a hydration material or a biological material.

17. The method of claim 12, further comprising selecting a graft tube from a set of graft tubes prior to loading the graft into the graft tube.

18. The method of claim 12, further comprising attaching the attachable to the graft tube prior to loading the graft into the graft tube.

19. A graft tube assembly, comprising:
a transparent body having a proximal end, a distal end, an outer diameter, and an inner diameter, wherein the inner diameter defines a hollowed tunnel configured to receive a graft;
an etched ruler on the transparent body;
a funneled entrance at the proximal end;
a tapered tip at the distal end; and
a plurality of perforations along a length of the transparent body.

20. The graft tube assembly of claim 19, further comprising an attachable handle.

21. A graft tube assembly, comprising:
a transparent body extending between a proximal end and a distal end and including an outer diameter and an inner dimeter, the inner diameter including a hollow tunnel;
a funneled entrance at the proximal end;
a tapered tip at the distal end;
a handle attachable to a head of the transparent body at the proximal end, the head having a diameter larger than the outer diameter of the transparent body, wherein the handle is rotatable in a first direction to lock the attachable handle to the head and is rotatable in a second, opposite direction to unlock the attachable handle from the head; and
a graft positioned within the hollow tunnel, wherein the graft is sized such that the inner diameter of the transparent body compresses the graft.

22. The graft tube assembly of claim 21, wherein the graft is a soft tissue graft having a length that can be measured using a ruler provided on the transparent body.

23. The graft tube assembly of claim 21, wherein the graft is a composite femoral bone/tendon allograft.

* * * * *